(12) United States Patent  
Wakana et al.

(10) Patent No.: US 7,362,033 B2  
(45) Date of Patent: Apr. 22, 2008

(54) SURFACE-ACOUSTIC-WAVE DEVICE

(75) Inventors: Shinichi Wakana, Kawasaki (JP); Akinori Miyamoto, Kawasaki (JP); Satoru Matsuda, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 11/365,655

(22) Filed: Mar. 2, 2006

(65) Prior Publication Data

US 2006/0146314 A1 Jul. 6, 2006

Related U.S. Application Data

(62) Division of application No. 10/406,268, filed on Apr. 4, 2003, now Pat. No. 7,054,005.

(30) Foreign Application Priority Data

Apr. 11, 2002 (JP) .............................. 2002-109571  
Dec. 26, 2002 (JP) .............................. 2002-376742

(51) Int. Cl.  
*H01L 41/08* (2006.01)  
*H03H 9/64* (2006.01)

(52) U.S. Cl. .............................. 310/313 D; 310/313 B

(58) Field of Classification Search ............ 310/313 R, 310/313 B, 313 D  
See application file for complete search history.

(56) References Cited

U.S. PATENT DOCUMENTS

| | | | | |
|---|---|---|---|---|
| 3,680,007 A | * | 7/1972 | Tseng | ........................ 333/154 |
| 3,836,876 A | * | 9/1974 | Marshall et al. | ............. 333/111 |
| 4,028,649 A | * | 6/1977 | Komatsu et al. | ............. 333/194 |
| 4,203,082 A | * | 5/1980 | Tsukamoto et al. | .......... 333/194 |
| 4,263,569 A | * | 4/1981 | Moellmer | .................... 333/151 |
| 4,659,923 A | | 4/1987 | Hicks, Jr. | |
| 4,727,275 A | * | 2/1988 | Milsom | .................... 310/313 D |
| 5,012,668 A | * | 5/1991 | Haworth | ..................... 73/24.06 |
| 5,064,270 A | | 11/1991 | Turpin et al. | |

(Continued)

FOREIGN PATENT DOCUMENTS

JP 5-503862 6/1993

OTHER PUBLICATIONS

Optical Waves in Crystals by Yariv, Yeh, Wiley-Interscience, 1983, p. 77.

*Primary Examiner*—Hezron Williams  
*Assistant Examiner*—Rose M Miller  
(74) *Attorney, Agent, or Firm*—Staas & Halsey LLP

(57) ABSTRACT

A surface-acoustic-wave device includes a piezoelectric substrate and first and second comb-shaped electrodes each having a bus-bar portion parallel to a propagation direction of a surface acoustic wave in the substrate. Respective electrode fingers are periodically formed on the piezoelectric substrate and extend in directions perpendicular to the propagation direction, wherein the electrode fingers of the first comb-shaped electrode and the electrode fingers of the second comb-shaped electrode are separated away from the bus-bar portion of the opposing comb-shaped electrode. The respective electrode fingers being periodically arrayed in the propagation direction of the surface-acoustic-wave, and the electrode fingers of each comb-shaped electrode are inclined at root portions thereof outwardly right and left from the bus-bar portion of the corresponding comb-shaped electrode so that the inclined portions of the electrode fingers face a direction of a leaking surface-acoustic-wave perpendicularly.

6 Claims, 15 Drawing Sheets

U.S. PATENT DOCUMENTS

| | | |
|---|---|---|
| 5,297,436 A | 3/1994 | Chan et al. |
| 5,460,048 A | 10/1995 | Chiang et al. |
| 5,670,920 A * | 9/1997 | Morgan ..................... 333/195 |
| 6,628,389 B1 | 9/2003 | Akada et al. |
| 6,927,853 B2 | 8/2005 | Geiler et al. |

* cited by examiner

SURFACE-ACOUSTIC-WAVE DEVICE

This application is a divisional of application Ser. No. 10/406,268, filed Apr. 4, 2003 now U.S. Pat. No. 7,054,005, now allowed.

CROSS-REFERENCE TO RELATED APPLICATIONS

This application is based on Japanese priority application No. 2002-109571, filed on Apr. 11, 2002, and Japanese priority application No. 2002-376742, filed on Dec. 26, 2002, the entire contents of which are hereby incorporated by reference.

BACKGROUND OF THE INVENTION

1. Field of the Invention

The present invention relates to an elastic-wave monitoring device which monitors the distribution of an elastic wave by performing measurement using a laser light, and to a surface-acoustic-wave device for use with the elastic-wave monitoring device.

2. Description of the Related Art

SAW (surface acoustic wave) devices and related components which utilize an elastic wave, such as a surface acoustic wave, have been briskly developed. In order to study the behavior of the SAW devices and use it for improvement of the SAW devices, there is an increasing demand for the technique to observe the elastic wave.

For example, there is known the technique which uses the interferometer to observe the distribution of a surface acoustic wave in a SAW device.

By this technique, the surface displacement of the surface acoustic wave is measured from a small change of optical intensity of a coupled light beam, which is obtained by using interference of a light beam reflected by the surface of the measured object and a light beam reflected by the reference mirror. Based on the principle that the displacement in the direction perpendicular to the surface changes the optical path difference, the surface displacement of the surface-acoustic-wave in the direction perpendicular to the surface is measured by this technique.

On the other hand, a conceivable method to observe the on-surface displacement of the measured object is to monitor the elastic-optical effects (stress birefringence) produced by distortion of the surface acoustic wave, by detecting a change of a polarization state of a transmission light through the measured object.

A polarization microscope is used to observe the stress distortion in the measured object from the double refraction by the elastic-optical effects. In addition, by using the composition that is the same as the optical modulator using the electro-optic effects, it is possible to detect the double refraction from the optical intensity change conversely.

In addition, Japanese Laid-Open Patent Application No. 5-503862 discloses an ultrasonic sensor which receives the incoming circularly polarized light at the polarization-holding-type fiber and outputs the degree of mode coupling excited by the incident supersonic wave.

By the method which performs the measurement using the interferometer, only the perpendicular displacement of the surface acoustic wave in the direction perpendicular to the surface of the measured object can be measured.

However, the surface acoustic wave used by the SAW device is composed of not only the perpendicular displacement but also the on-surface displacement. Actually, the SAW device using a 36-degree Y cut plate of lithium tantalate ($LiTaO_3$) crystal shows almost only the on-surface displacement. Otherwise, it uses the surface acoustic wave in which the overall energy is created by the on-surface displacement. Therefore, the measurement method using the interferometer is not suitable for observing the distribution of the surface acoustic wave in such a SAW device.

When considering the detection of the elastic-optical effects (stress birefringence) from a change of a polarization state of transmission light in order to observe the on-surface displacement, the crystal substrate of the SAW device has the optical anisotropy and the surface of the crystal substrate is a cut plane having a complicated angle. With a simple composition like the optical modulator utilizing the electro-optic effects, it is difficult to perform the observation of the surface acoustic wave in the actual SAW device.

FIG. 1 shows a conventional elastic-wave monitoring device. In FIG. 1, only the composition of the optical system of the conventional elastic-wave monitoring device is shown. The conventional elastic-wave monitoring device monitors refractive index change produced by the elastic-optical effects, by detecting a change of a polarization state of a transmission light. The composition of FIG. 1 is used for an optical modulator or the like.

In the optical system shown in FIG. 1, the circularly polarized light 2 from the light source is incident to the crystal 3 that is a measured object. The light 2 passes through the crystal 3, and further passes through the phase-difference compensating plate 4 and the polarizing filter 41, in this order. The resulting light from the polarizing filter 41 is incident to the photodetector 6.

Suppose that the X-axis 14 and the Y-axis 15 are predetermined with respect to the propagation direction of light so that the index of refraction of the crystal 3 is defined. The refractive index of the crystal 3 is composed of the x-axis direction component "nx" and the y-axis direction component "ny".

FIG. 2A and FIG. 2B are diagrams for explaining the relation of a change of polarization to a change of refractive index in the optical system of FIG. 1.

As shown in FIG. 2A, the circularly polarized light is converted into the elliptically polarized light having the principal axis in the direction of 45 degrees, due to the change Δn of the refractive index in the x-axis direction.

The optical intensity I (indicated by the distance of the line 46 and the origin of the index ellipsoid shown in FIG. 2B) of the 45-degree direction polarization component is represented by the formula:

$I = Io + C\Delta n$ (where Io is the intensity when there is no change of the refractive index, and C is a factor).

In the composition of FIG. 1, the polarizing filter 41 has the transmission axis 42 in the 45-degree direction. The optical intensity of the polarized light from the polarizing filter 41 is indicated by the optical intensity I mentioned above.

As shown in FIG. 2B, the sensitivity of the optical intensity of the polarized light from the polarizing filter 41 is the maximum when the direction of the transmission axis 42 of the polarizing filter 41 is the 45-degree direction between the X axis and the Y axis which are used to define the index of refraction of the crystal 3. In the 0-degree direction, the optical intensity is not sensitive.

As the anisotropic crystal has the index of refraction that varies with the propagation direction of the transmission light, the index of refraction is determined for each of the directions of the principal axes of an ellipse formed by intersections of the index ellipsoid of the crystal and a plane perpendicular to the propagation direction of the transmission light and passing through the origin of the index ellipsoid. The magnitude of the index of refraction is indicated by the length of one of the principal axes of the ellipse.

When the elastic-optical effects occur, the index ellipsoid is deformed and it serves as a change of the index of refraction to the light in an arbitrary propagation direction. The final change of the index of refraction is determined with the distortion component of the surface acoustic wave, the elastic-optical effects and the propagation direction of light. The change, which is detected with the composition of FIG. 1, does not necessarily appear with sufficient convenience.

FIG. 3A and FIG. 3B are diagrams for explaining the relation of a change of polarization to a change of the direction by which a refractive index is defined.

When the crystal 3 as the measured object is provided in the form of a 36-degree Y cut plate of a lithium tantalate crystal, and the light is incident to the cut surface of the crystal 3 at right angles to the cut surface, it is found that the axes by which the index of refraction is defined are rotated as shown in FIG. 3A. However, the value of the index of refraction itself does not substantially change. It is difficult for the conventional elastic-wave monitoring device of FIG. 1 to detect a change of the surface acoustic wave in such a case.

Moreover, although it is possible for the conventional elastic-wave monitoring device of FIG. 1 to observe the distribution of the elastic wave in the SAW device, there is the problem that the behavior of the elastic wave in a non-sensitive range of the SAW device in which the light does not penetrate the SAW device cannot be observed. The non-sensitive range is, for example, the range of the SAW device in which the metal electrode is formed on the crystal substrate.

The metal electrode on the SAW device functions as the mirror to reflect the incident light. Hence, the light incident to the metal-electrode range of the SAW device is reflected, and the metal-electrode range becomes the non-sensitive range in which the incident light does not interact with the crystal substrate of the SAW device.

SUMMARY OF THE INVENTION

An object of the present invention is to provide an improved elastic-wave monitoring device in which the above-described problems are eliminated.

Another object of the present invention is to provide an elastic-wave monitoring device which is capable of appropriately monitoring the on-surface displacement of an elastic wave in a crystal substrate of a SAW device which has the optical anisotropy and the cut plane with a complicated angle.

Another object of the present invention is to provide an elastic-wave monitoring device and method which is capable of precisely monitoring the behavior of an elastic wave in all the ranges of the crystal substrate of the SAW device without any non-sensitive region.

The above-mentioned objects of the present invention are achieved by an elastic-wave monitoring device comprising: an optical system arranged so that a circularly polarized light from a light source is incident to a measured object and a light beam from the measured object passes through a polarizing filter to a photodetector; and a detection unit detecting periodic fluctuation components of an output signal of the photodetector, wherein the polarizing filter is arranged to have a polarization transmission axis directed to one of directions of principal axes of an ellipse formed by intersections of an index ellipsoid of the measured object and a plane perpendicular to an incidence direction of the light beam and passing through an origin of the index ellipsoid.

The above-mentioned objects of the present invention are achieved by an elastic-wave monitoring device comprising: an optical system arranged so that a circularly polarized light from a light source is separated into a first light beam incident to a measured object and a second light beam incident to a reference mirror by a beam splitter, a light beam from the measured object passes through a polarizing filter to a first photodetector, and a coupled light beam is generated from a reflected beam from the measured object and a reflected beam from the reference mirror by the beam splitter so that the coupled light beam is received by a second photodetector; a first detection unit detecting periodic fluctuation components of an output signal of the first photodetector; a second detection unit detecting periodic fluctuation components of an output signal of the second photodetector; and a computation unit performing computations based on outputs of the first and second detection units, wherein the polarizing filter is arranged to have a polarization transmission axis directed to one of directions of principal axes of an ellipse formed by intersections of an index ellipsoid of the measured object and a plane perpendicular to an incidence direction of the first light beam and passing through an origin of the index ellipsoid.

According to the elastic-wave monitoring device of the present invention, it is possible to appropriately monitor the on-surface displacement of an elastic wave in the measured object, such as a SAW device, which has not been observed with the conventional elastic-wave monitoring device mentioned above.

The above-mentioned objects of the present invention are achieved by a surface-acoustic-wave device comprising: a piezoelectric substrate; and first and second comb-shaped electrodes each having a bus-bar portion parallel to a propagation direction of a surface acoustic wave in the substrate, and respective electrode fingers periodically formed on the piezoelectric substrate and extending in directions perpendicular to the propagation direction, wherein the electrode fingers of the first comb-shaped electrode and the electrode fingers of the second comb-shaped electrode are separated away from the bus-bar portion of the opposing comb-shaped electrode, the respective electrode fingers being periodically arrayed in the propagation direction of the surface-acoustic-wave, and the electrode fingers of each comb-shaped electrode are inclined at root portions thereof outwardly right and left from the bus-bar portion of the corresponding comb-shaped electrode so that the inclined portions of the electrode fingers face a direction of a leaking surface-acoustic-wave perpendicularly.

The above-mentioned objects of the present invention are achieved by a surface-acoustic-wave device comprising: a piezoelectric substrate; an inter-digital transducer provided on the piezoelectric substrate, the inter-digital transducer including first and second comb-shaped electrodes each having a bus-bar portion parallel to a propagation direction of a surface acoustic wave in the substrate, and respective electrode fingers periodically formed on the piezoelectric substrate and extending in directions perpendicular to the propagation direction; and a pair of reflectors provided at a left edge and a right edge of the inter-digital transducer along the propagation direction, wherein the electrode fingers of the first comb-shaped electrode and the electrode fingers of the second comb-shaped electrode are separated away from the bus-bar portion of the opposing comb-shaped electrode, the respective electrode fingers being periodically arrayed in the propagation direction of the surface-acoustic-wave, and the electrode fingers of each comb-shaped electrode are inclined at root portions thereof outwardly right and left from the bus-bar portion of the corresponding comb-shaped electrode so that the inclined portions of the electrode fingers face a direction of a leaking surface-acoustic-wave perpendicularly.

According to the surface-acoustic-wave device of the present invention, the surface-acoustic-wave energy which has leaked out of the comb-shaped electrodes as in the conventional SAW device can be reduced, and it is possible to improve the electrical properties of the surface-acoustic-wave device.

The above-mentioned objects of the present invention are achieved by an elastic-wave monitoring device comprising: a piezoelectric substrate having a first surface where a metal electrode is formed on a piezoelectric crystal, and a second surface being ground and opposing to the first surface; a first polarization-analysis optical system arranged so that a light beam from a light source is incident to the second surface of the substrate when the electrode on the first surface is excited by a driving voltage, and a reflected light beam from an interface between the electrode and the piezoelectric crystal on the first surface of the substrate is received by a first photodetector; and a detection unit detecting a change of a polarization state of the reflected light beam received by the first photodetector of the first polarization-analysis optical system to monitor a distribution of an elastic wave in the substrate.

The above-mentioned objects of the present invention are achieved by an elastic-wave monitoring method comprising the steps of: providing a piezoelectric substrate having a first surface where a metal electrode is formed on a piezoelectric crystal, and a second surface being ground and opposing to the first surface; arranging a first polarization-analysis optical system so that a light beam from a light source is incident to the second surface of the substrate when the electrode on the first surface is excited by a driving voltage, and a reflected light beam from an interface between the electrode and the piezoelectric crystal on the first surface of the substrate is received by a first photodetector; and detecting a change of a polarization state of the reflected light beam received by the first photodetector of the first polarization-analysis optical system to monitor a distribution of an elastic wave in the substrate.

According to the elastic-wave monitoring device and method of the present invention, it is possible to monitor the distribution of an elastic wave in all the ranges of the measured object, such as the SAW device, without any non-sensitive region, and to observe the behavior of the elastic wave more precisely.

BRIEF DESCRIPTION OF THE DRAWINGS

Other objects, features and advantages of the present invention will be apparent from the following detailed description when read in conjunction with the accompanying drawings.

DETAILED DESCRIPTION OF PREFERRED EMBODIMENTS

A description will now be given of preferred embodiments of the present invention with reference to the accompanying drawings.

Figure 5:
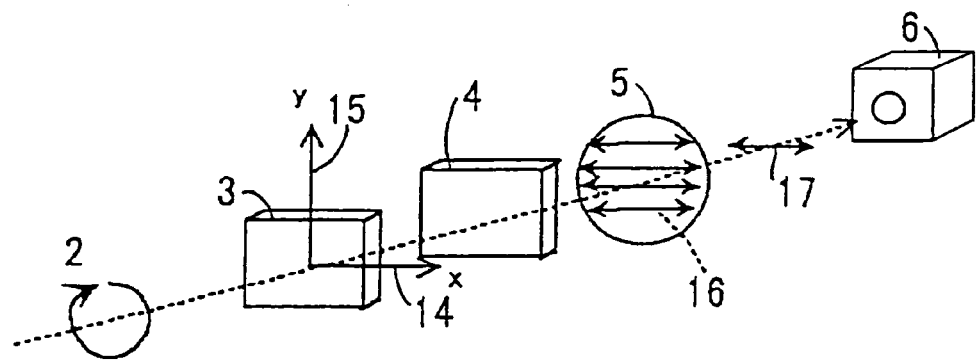
FIG. 5 is a diagram showing a basic configuration of the elastic-wave monitoring device of the present invention.
Figure 6:
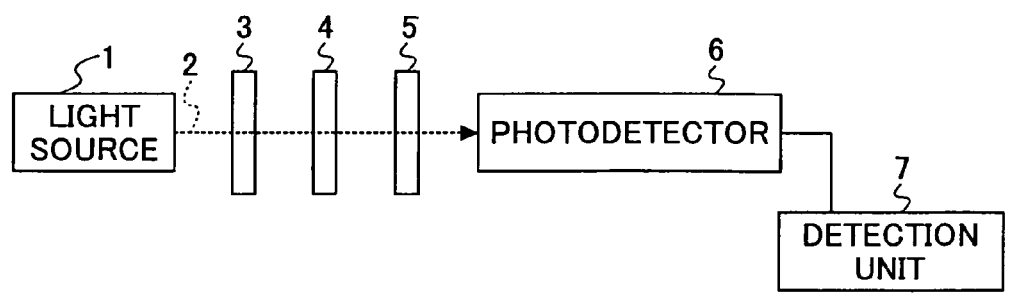
FIG. 6 is a block diagram of one preferred embodiment of the elastic-wave monitoring device of the present invention.

FIG. 5 shows a basic configuration of the elastic-wave monitoring device of the present invention. FIG. 6 shows the elastic-wave monitoring device in one preferred embodiment of the present invention.

In the elastic-wave monitoring device of FIG. 5, the circularly polarized light 2 from the light source is incident to the crystal 3 that is a measured object. The light 2 passes through the crystal 3, and further passes through the phase-difference compensating plate 4 and the polarizing filter 5, in this order. The resulting light from the polarizing filter 5 is received by the photodetector 6.

In the composition of FIG. 5, the polarizing filter 5 is arranged to have a polarization transmission axis 16 directed to one (as indicated by the arrow 17) of the directions of the principal axes of an ellipse formed by intersections of the index ellipsoid of the crystal 3 and a plane perpendicular to the incidence direction of the light beam and passing through the origin of the index ellipsoid.

The elastic-wave monitoring device of the present invention monitors the double refraction-produced by the elastic-optical effects, by detecting a change of a polarization state of a transmission light through the measured object 3.

In the optical system of the elastic-wave monitoring device of FIG. 6, the circularly polarized light 2 from the light source 1 is incident to the measured object 3, and the light 2 passes through the measured object 3, and further passes through the phase-difference compensating plate 4 and the polarizing filter 5, in this order. The resulting light from the polarizing filter 5 is received by the photodetector 6.

In the elastic-wave monitoring device of FIG. 6, the detection unit 7 is connected to the output of the photodetector 6 of the above-mentioned optical system.

The periodic fluctuation component of the double refraction produced by the surface-acoustic-wave appears in the output of the photodetector 6, and the detection unit 7 detects the periodic fluctuation component of this output, and monitors the optical intensity of the elastic wave.

As shown in FIG. 5, in the elastic-wave monitoring device of this embodiment, the direction 16 of the polarization transmission axis of the polarizing filter 5 is in agreement with one of the directions 14 and 15 of the principal axes of the ellipse formed by the intersections of the index ellipsoid and the plane perpendicular to the incidence direction of the light beam and passing through the origin of the index ellipsoid.

In the composition of FIG. 5, the phase-difference compensating plate 4 is provided to compensate for the natural double refraction of the substrate portion of the measured object 3.

Figure 1:
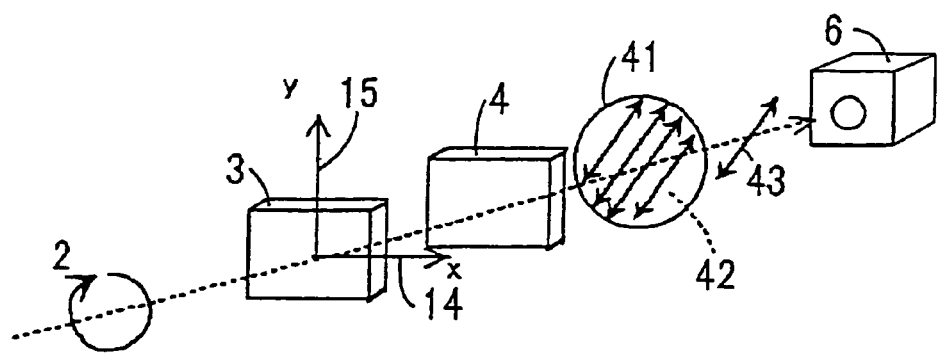
FIG. 1 is a diagram showing a conventional elastic-wave monitoring device.
Figure 2A:
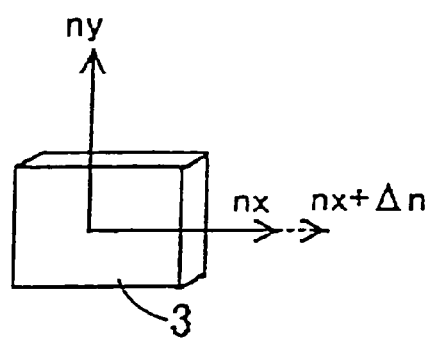
FIG. 2A and FIG. 2B are diagrams for explaining the relation of a change of polarization to a change of refractive index.
Figure 2B:
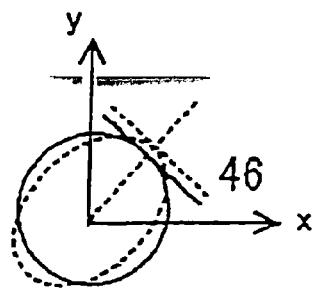
Figure 3A:
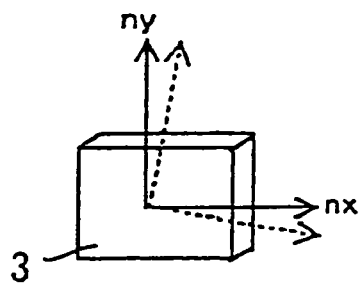
FIG. 3A and FIG. 3B are diagrams for explaining the relation of a change of polarization to a change of the direction by which a refractive index is defined.

As a result of the study on the composition for detecting the change as shown in FIG. 3A, it is found suitable that the incident light 2 is circularly polarized light and the transmission axis 16 of the polarizing filter 5 is directed to the X-axis 14 (or the Y-axis 15) with which the index of refraction of the crystal becomes settled as in the composition of FIG. 5.

In addition, the X-axis 14 changes the direction by the elastic-optical effects, but the change is minute and it is not necessary to distinguish especially the direction which makes in agreement with the transmission axis 16 of the polarizing filter 5 before or after the rotation.

Figure 3B:
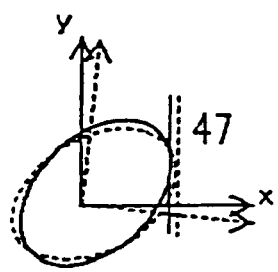

Since the circularly polarized light turns into the elliptical polarization for the natural double refraction (in which nx differs from ny) of the range where the surface-acoustic-wave has occurred and the sense of the main axis of this elliptical polarization rotates in connection with the X-axis 14 and the Y-axis 15 by which the index of refraction becomes settled, as the polarization state at this time is shown in FIG. 3B, it appears as a change of the polarization component intensity in the x-axis direction (indicated by the distance between the line 47 and the origin of the index ellipsoid in FIG. 3B).

Figure 4A:
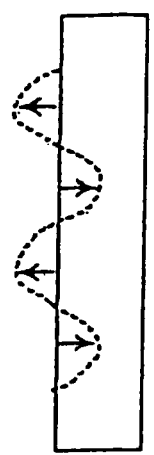
FIG. 4A and FIG. 4B are diagrams for explaining displacement components of a surface acoustic wave.
Figure 4B:
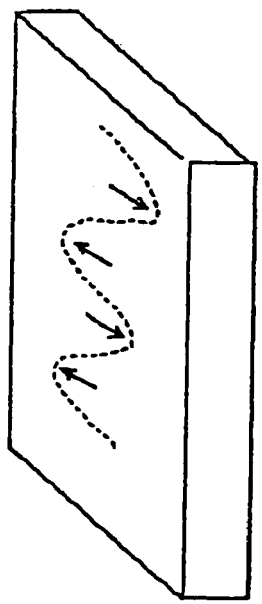
Figure 7:
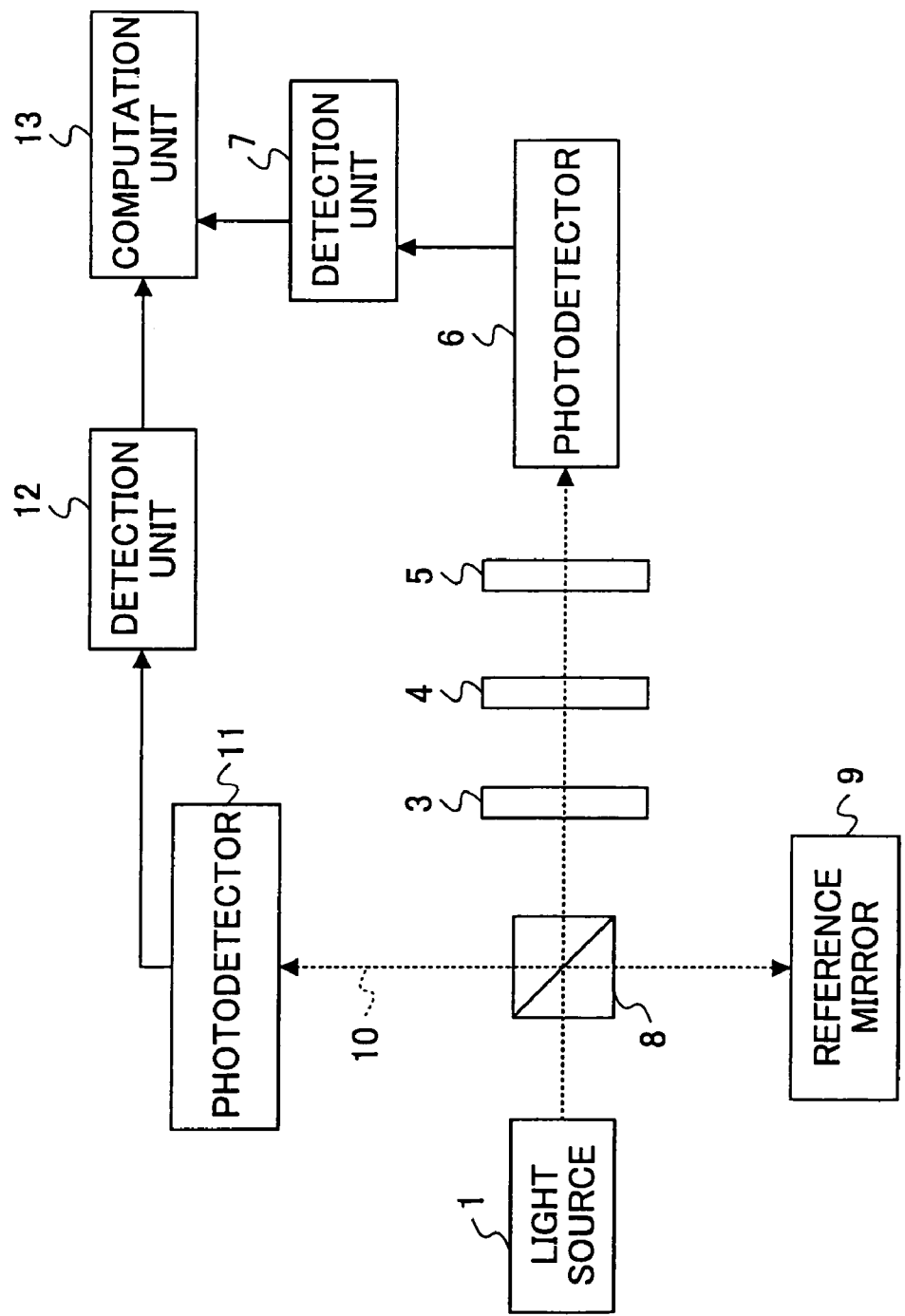
FIG. 7 is a block diagram of another preferred embodiment of the elastic-wave monitoring device of the present invention.

FIG. 7 shows the elastic-wave monitoring device in another embodiment of the present invention. FIG. 4A and FIG. 4B are diagrams for explaining the displacement components of the surface acoustic wave.

There are the on-surface component and the vertical component among the displacement components of the surface wave as shown in FIG. 4A and FIG. 4B.

To observe the distribution of the on-surface component only as the surface wave has both the components, taking a suitable measure is needed. The measurement of the on-surface component is associated with the measurement by the interferometer which measures the vertical component as shown in FIG. 7.

The measurement of the perpendicular displacement by the interferometer can be performed by determining the magnitude of the periodic fluctuation component of the output of the photodetector 11 by the detection unit 12. The contribution of only the on-surface-displacement component can be determined by deducting this from the output of the detection unit 7 which indicates the intensity of the surface-acoustic-wave in the polarization detection by the computation unit 13.

In the elastic-wave monitoring device of FIG. 7, the optical system is arranged so that the circularly polarized light from the light source 1 is separated into a first light beam incident to the measured object 3 and a second light beam incident to the reference mirror 9 by the beam splitter 8, and a light beam from the measured object 3 passes through the phase-difference compensating plate 4 and the polarizing filter 5 to the photodetector 6.

In the elastic-wave monitoring device of FIG. 7, after the transmission light through the measured object 3 passes through the phase-difference compensating plate 4 and the polarizing filter 5 in this order, it is received by the photodetector 6.

Moreover, similar to the composition of FIG. 5, the direction 16 of the polarization transmission axis of the polarizing filter 5 is in agreement with one of the directions 14 and 15 of the principal axes of the ellipse formed by the intersections of the index ellipsoid and the plane perpendicular to the incidence direction of the light beam and passing through the origin of the index ellipsoid.

Moreover, in the elastic-wave monitoring device of FIG. 7, a coupled light beam is generated from a reflected beam from the measured object 3 and a reflected beam from the reference mirror 9 by the beam splitter 8 so that the coupled light beam is received by the photodetector 11.

Furthermore, the elastic-wave monitoring device of FIG. 7 is provided with the detection unit 7 which detects the periodic fluctuation components of the output signal of the photodetector 6, the detection unit 12 which detects the periodic fluctuation components of the output signal of the photodetector 11, and the computation unit 13 which carries out computations based on both the output of the detection unit 7 and the output of the detection unit 12.

In the elastic-wave monitoring device of FIG. 7, when the measured object 3 is the surface-acoustic-wave device which utilizes surface acoustic wave of the on-surface type, an electrical signal having a frequency at which resonance of surface acoustic wave of Rayleigh type occurs is applied to the measured object 3. The computation unit 13 determines a correction factor for the output of the detection unit 12 based on the condition that the output of the detection unit 12 of multiplied by the correction factor is equal to the output of the detection unit 12.

In the computation unit 13 of this embodiment, when deducting the output of the detection unit 12, which indicates the signal value acquired with the interferometer, from the output value of the detection unit 7, it is necessary to determine the correction factor by which the output of the detection unit 12 is multiplied.

That is, the signal Sint acquired with the interferometer and multiplied by the correction factor is reduced from the signal Spol acquired by the polarization detection, and the resulting signal Sp is calculated by the following formula, which indicates the contribution to the polarization detection by the on-surface component:

$Sp=Spol-Sint \times D$ (D: correction factor)

Although it can be determined from the theoretical sensibility calculation, the above-mentioned method of determining the correction factor D experimentally is provided because the actual optical system is not ideal for conforming to the theoretical sensibility calculation.

In order to determine the correction factor, even if it is the device designed so that the on-surface displacement of the elastic wave is used, the method using the resonance of the Rayleigh wave and determining the correction factor is effective.

In the SAW device, the metal electrode having the periodic configuration is formed and the resonance frequency thereof can be determined by the following formula from the speed of the elastic wave, and the periodicity of the electrode.

$fr=V/\lambda s$ where fr indicates the resonance frequency, $\lambda s$ indicates the periodicity of the electrode, and V indicates the speed of the elastic wave.

When the measured object is designed to use the on-surface type surface wave, the speed of the on-surface type surface wave is used as "V" of the above formula.

Even if the measured object is not designed apart from this so that the SAW device may excite the Rayleigh wave if the electrical signal of frequency f' which the Rayleigh wave may exist and can be determined by the formula: $f'=Vr/\lambda s$ from the speed Vr of the Rayleigh wave applied to the electrode, the large Rayleigh wave may be excited.

Generally, the displacement of the surface wave is composed of the three components: the SV component which is perpendicular to the surface of the measured object, the P component which is the longitudinal wave component of the on-surface displacement, and the SH component which is the transverse-wave component of the on-surface displacement. The Rayleigh wave is composed of the SV component and the P component.

In order to determine the above-mentioned correction factor when the polarization detection senses the contributions by the SH component and the SV component, it is appropriate to determine the correction factor by using the following formula, from the signal Sint' obtained by the interferometer and the signal Spol' obtained by the polarization detection measurement when generating the Rayleigh wave:

Correction factor=$Spol'/Sint'$.

Figure 8:
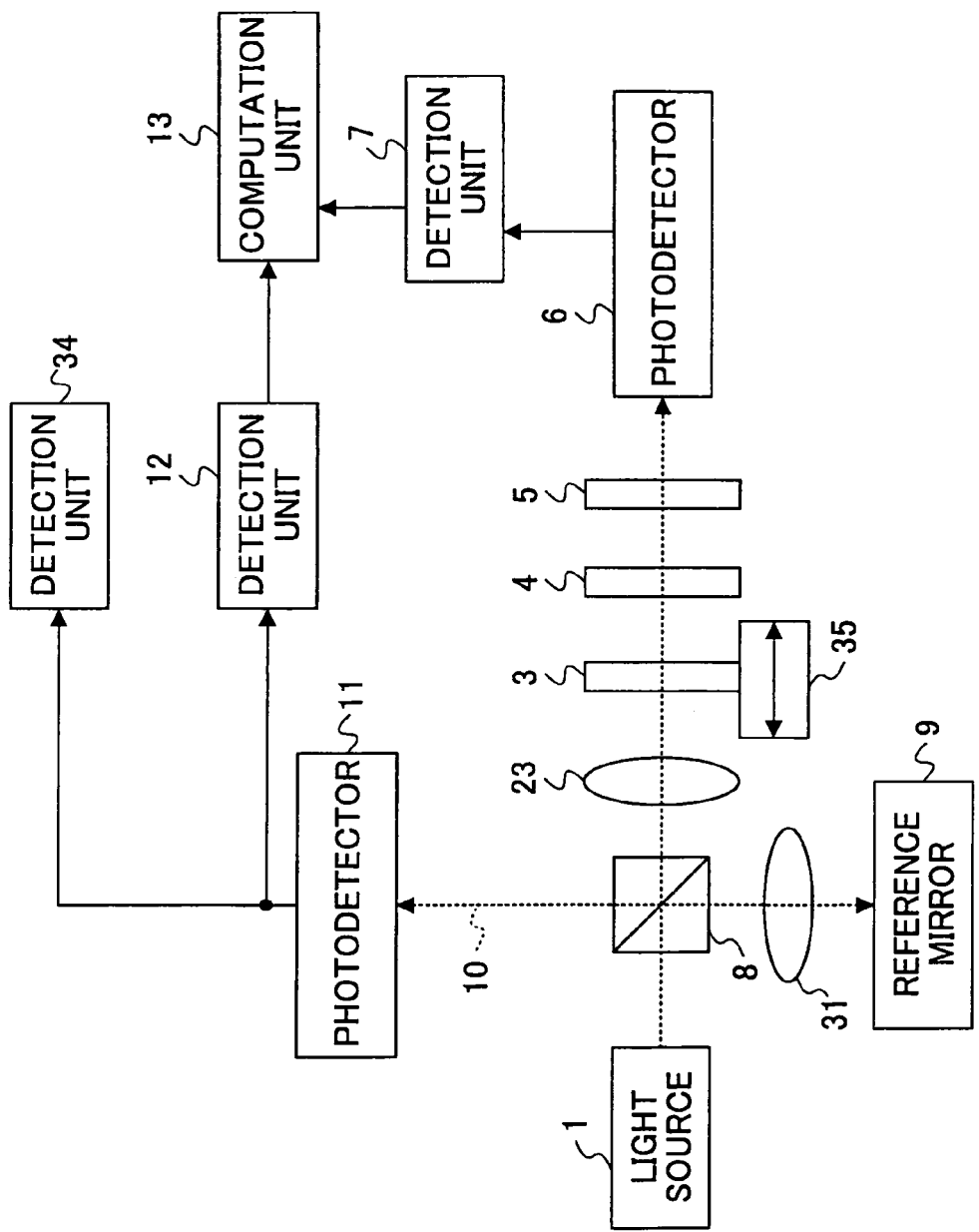
FIG. 8 is a block diagram of another preferred embodiment of the elastic-wave monitoring device of the present invention.
Figure 9:
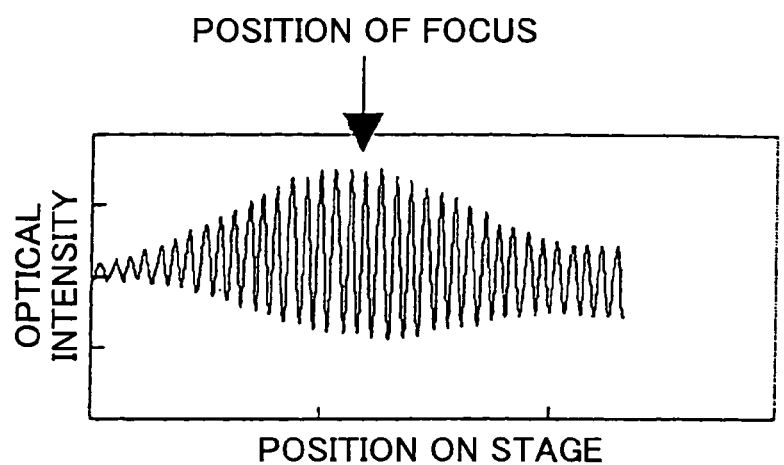
FIG. 9 is a diagram for explaining changes of optical intensity of a coupled light beam in accordance with the position of the measured object on the stage.

Next, FIG. 8 shows the elastic-wave monitoring device in another embodiment of the present invention. FIG. 9 is a diagram for explaining changes of optical intensity of a coupled light beam in accordance with the position of the measured object on the stage.

In the elastic-wave monitoring device shown in FIG. 8, one of the light beams which are separated by the beam splitter 8 passes through the lens 23 and it is incident to the front surface of the measured object 3. The other light beam from the beam splitter 8 passes through the lens 31 and it is incident to the reference mirror 9.

The measured object 3 is attached to the stage 35 which is movable in the direction so as to change the distance from the lens 23. Moreover, as for the reference mirror 9, the position thereof is adjusted so that the front surface of the mirror serves as the focal position of the lens 31.

In the elastic-wave monitoring device of FIG. 8, the photodetector 11 outputs the signal which indicates the optical intensity of the coupled light beam 10, which is obtained from both a reflected light beam from the front surface of the measured object 3 and a reflected light beam from the reference mirror 9 when the measured object 3 is moved with the stage 35.

Moreover, the detection unit 34 which receives the output of the photodetector 11 is provided in the elastic-wave monitoring device of FIG. 8, and the detection unit 34 is a circuit capable of detecting a position of a maximum intensity change caused by interference of the light wave. In the elastic-wave monitoring device of this embodiment, the position of the stage 35 may be adjusted to the position of the maximum intensity change detected by the detection unit 34.

When measuring the elastic wave, especially the surface acoustic wave, by the elastic-wave monitoring device of this embodiment, the light beam is focused on the measured object front surface with the focus spot diameter being smaller than the wavelength of the surface acoustic wave by using the lenses. Hence, the elastic-wave monitoring device of this embodiment is desirable to monitor the distribution of the surface acoustic wave.

It is necessary to adjust the position of the front surface of the measured object so that it may be in agreement with the focal location of the lens. Such efficient approach using the interferometer part is that the location where the maximum intensity change by interference of the light wave occurs in the output of the photodetector 11 is detected, and the position of the stage 35 is adjusted to the detected location of the maximum intensity change by moving the measured object 3 in the direction of the optical path with the stage 35.

As shown in FIG. 9, the changes of the optical intensity of the coupled light beam occur with the periodicity of $\lambda/2$ ($\lambda$: wavelength of the light) in accordance with the amount of stage movement.

If the reference mirror 9 is adjusted, in advance, to the focal location of the lens 31 and the front surface of the measured object 3 suits the focal location of the lens 23, the wave fronts of each reflected light beam overlap exactly in the beam splitter 8, which results in a high level of interference.

However, if the front surface of the measured object 3 is shifted from the focal location of the lens 23, the wave fronts will not overlap and the level of interference becomes low. Therefore, the position where the optical intensity change by interference is the maximum is the focal location.

Figure 10:
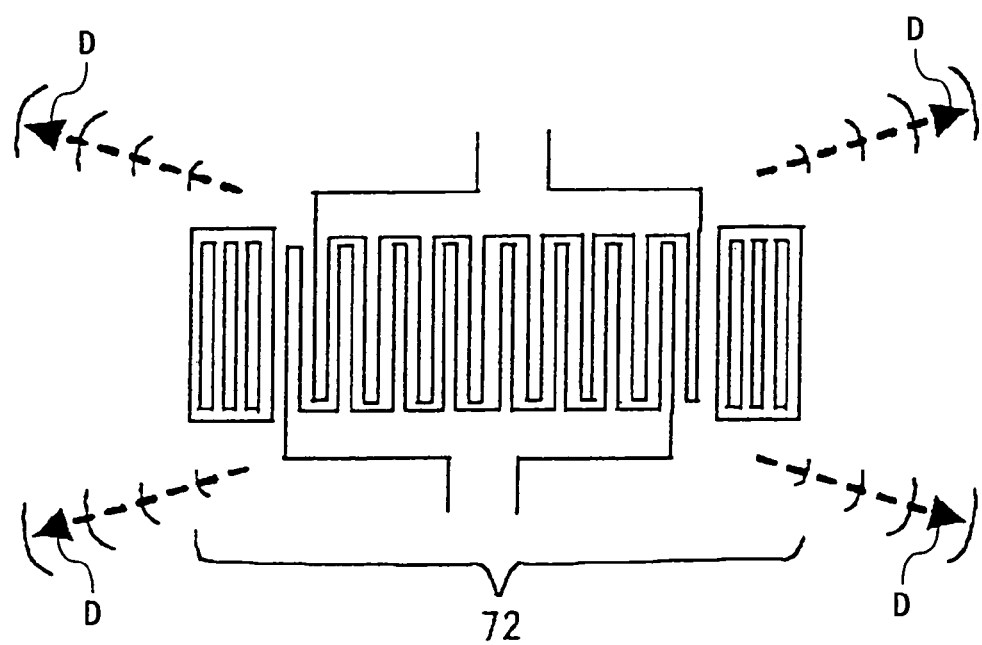
FIG. 10 is a diagram for explaining the distribution of leaking surface acoustic waves in a conventional surface-acoustic-wave device.
Figure 11:
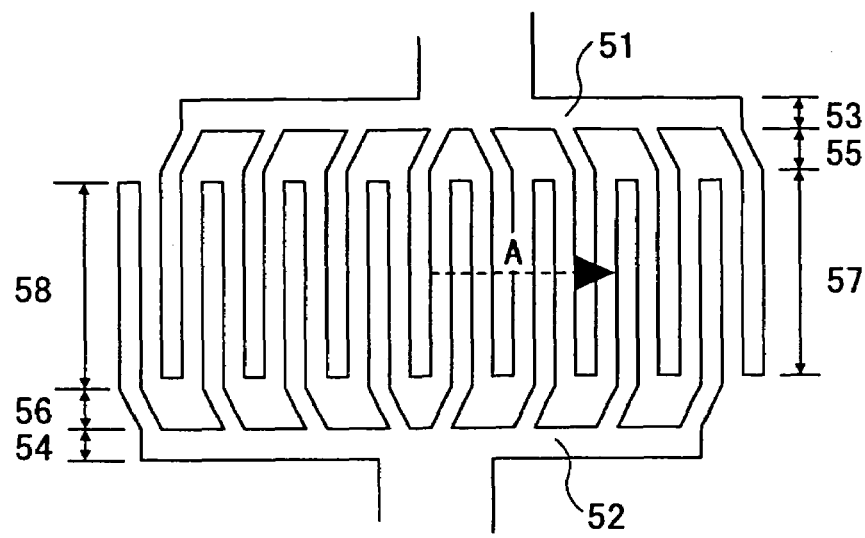
FIG. 11 is a diagram of an IDT electrode used in one embodiment of the surface-acoustic-wave device of the present invention.

Next, FIG. 10 is a diagram for explaining the distribution of the leaking surface acoustic waves in a conventional surface-acoustic-wave device. FIG. 11 shows an example of the IDT electrode used for the surface-acoustic-wave device of the present invention.

As shown in FIG. 10, when the elastic-wave monitoring device is used, it is observed that, in the resonator-type surface-acoustic-wave device 72, the surface acoustic wave has leaked in the directions D at fixed angles to the propagation direction of the surface acoustic wave.

Then, it is found that the leakage of the energy out of the SAW device can be reduced by forming the electrode fingers in the direction which intersects perpendicularly with the fixed directions D and reflecting the surface acoustic wave by the electrode fingers formed in the perpendicular direction.

The surface-acoustic-wave device of FIG. 11 comprises the piezoelectric substrate, and first and second comb-shaped electrodes 51 and 52 having respective bus-bar portions 53 and 54 parallel to the propagation direction (indicated by the arrow A in FIG. 11) of the surface acoustic wave in the substrate, and respective electrode fingers 57 and 58 periodically formed on the piezoelectric substrate and extending in directions perpendicular to the propagation direction, In the composition of FIG. 11, the electrode fingers 57 of the first comb-shaped electrode 51 and the electrode fingers 58 of the second comb-shaped electrode 52 are separated away from the bus-bar portion of the opposing comb-shaped electrode, the respective electrode fingers being periodically arrayed in the propagation direction of the surface-acoustic-wave, and the electrode fingers of each comb-shaped electrode are inclined at root portions 55 and 56 thereof outwardly right and left from the bus-bar portion of the corresponding comb-shaped electrode so that the inclined portions of the electrode fingers 57 and 58 face the directions (as indicated by the arrow D in FIG. 10) of the leaking surface-acoustic-wave perpendicularly.

According to the embodiment of FIG. 11, the root portions 55 and 56 of the comb-shaped electrodes 51 and 52 are inclined as described above, and the surface acoustic wave which is about to leak from the inclined portions is reflected by such inclined portions, so that the energy which leaks out of the SAW device can be reduced efficiently and the electrical properties of the SAW device can be increased.

Figure 12:
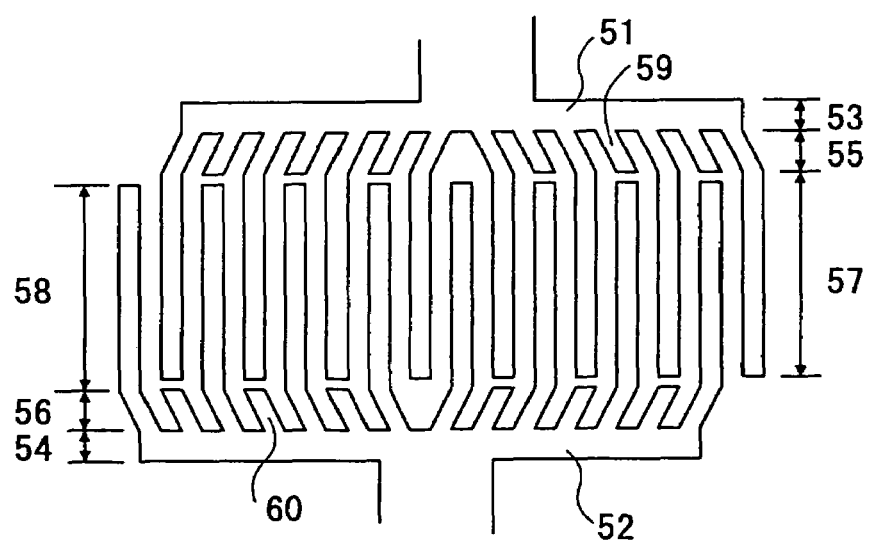
FIG. 12 is a diagram of another IDT electrode used in one embodiment of the surface-acoustic-wave device of the present invention.

FIG. 12 shows an example of the IDT electrode used in one embodiment of the surface-acoustic-wave device of the present invention.

In the surface-acoustic-wave device of FIG. 12, it connects with the bus-bar portion 53 of the first comb-shaped electrode 51, and the dummy electrodes 59 extended to this side at the nose of cam of the electrode finger of the second comb-shaped electrode 52 is formed in the intermediate valve position of each electrode finger of the first comb-shaped electrode 51.

Similarly, it connects with the bus-bar portion 54 of the second comb-shaped electrode 52, and the dummy electrode 60 extended to this side at the nose of cam of the electrode finger of the first comb-shaped electrode 51 is formed in the intermediate valve position of each electrode finger of the second comb-shaped electrode 52.

Moreover, in the surface-acoustic-wave device of FIG. 12, the dummy electrode 59 of the first comb-shaped electrode 51 is formed in the same direction as the root portion 55 of the electrode finger of the first surrounding comb-shaped electrode 51, and the dummy electrode 60 of the second comb-shaped electrode 52 is similarly formed in the same direction as the root portion 56 of the electrode finger of the second surrounding comb-shaped electrode.

Moreover, the piezoelectric substrate of LiTaO3 single crystal has a cut plane rotated around the X-axis by 36 to 46 degrees from the Y-axis to the Z-axis of the crystal, and the edge of each reflector is inclined by 8 to 15 degrees, and is made to form in the surface-acoustic-wave device of FIG. 12 from the direction which intersects perpendicularly with the direction A which is the propagation direction of the surface-acoustic-wave.

According to the embodiment of FIG. 12, reflective effectiveness can be improved and the discontinuity of the surface load with the part of root portions and the part with the parts 57 and 58 is avoidable by adding the dummy electrodes 59 and 60.

Figure 13:
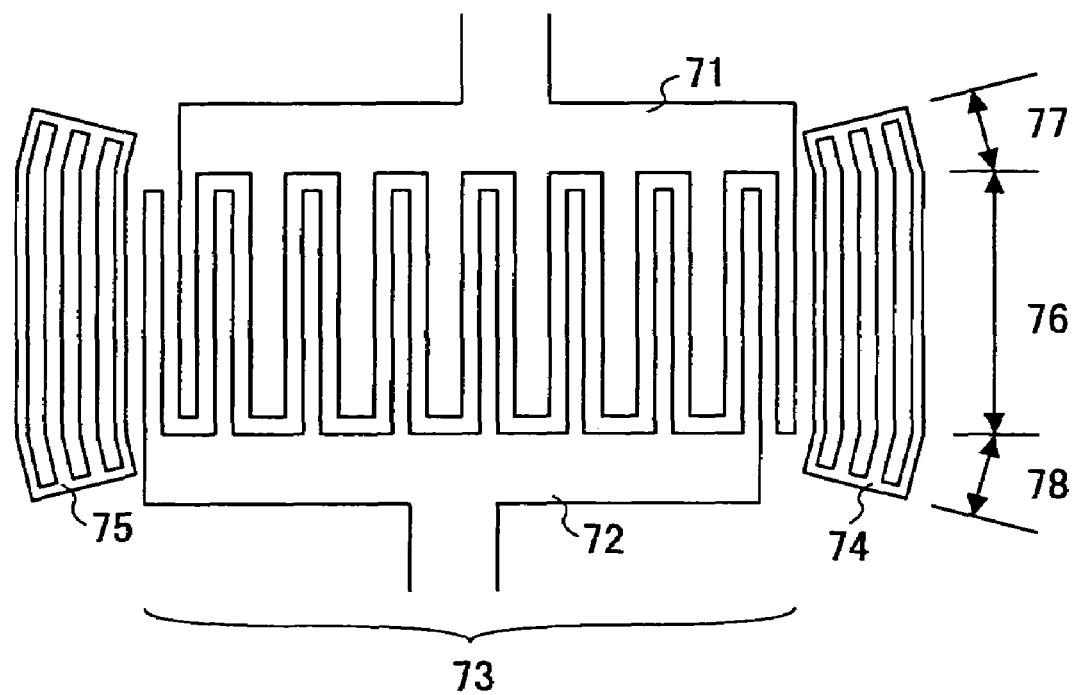
FIG. 13 is a diagram of another IDT electrode used in one embodiment of the surface-acoustic-wave device of the present invention.

FIG. 13 shows an example of the IDT electrode and reflectors used in one embodiment of the surface-acoustic-wave device of the present invention.

In the surface-acoustic-wave device of FIG. 13, the above-mentioned piezoelectric substrate, and the first comb-shaped electrode 71 and the second comb-shaped electrode 72 which are formed in the front surface of the piezoelectric substrate are put together, and the inter-digital transducer (IDT) 73 is formed.

It adjoins in the propagation direction (the direction A) of the surface-acoustic-wave of the IDT 73, and the reflectors 74 and 75 are arranged.

The reflectors 74 and 75 include the periodic electrode fingers, and each electrode finger has the center portion 76 extending in the direction perpendicular to the propagation direction (indicated by the arrow A in FIG. 11) of the surface acoustic wave, and having the edge portions 77 and 78 inclined at fixed angles to the propagation direction. The fixed inclination angles of the edges 77 and 78 are to intersect perpendicularly with the leaking surface-acoustic wave. The directions of the edges 77 and 78 are detectable with the elastic-wave monitoring device of the above-mentioned embodiment, and they are perpendicular to the directions in which the surface acoustic wave leaks out of the IDT 73.

Specifically, in the surface-acoustic-wave device of FIG. 13, at the edges 77 and 78 of the right-hand reflector 74, the fixed inclination angles are made in the leftward interior direction, and at the edges of the left-hand reflector 75, the fixed inclination angles is made in the rightward interior direction.

In the surface-acoustic-wave device of FIG. 13, the piezoelectric substrate of LiTaO3 single crystal has a cut plane rotated around the X-axis by 36 to 46 degrees from the Y-axis to the Z-axis of the crystal, and from the direction which intersects perpendicularly with the propagation direction of the surface-acoustic-wave, the edge portions of the reflectors 74 and 75 are inclined by 8 to 15 degrees.

As shown in FIG. 13, the edges of the reflectors 74 and 75 on the both sides of the IDT 73 are extended and inclined, apart from the conventional configuration of FIG. 10, and the inclination angles of such edges are to intersect perpendicularly with the radiation direction of the leaking surface acoustic wave. Therefore, the surface acoustic wave can safely propagate without large leakage and the effectiveness of the device can be raised.

Figure 14:
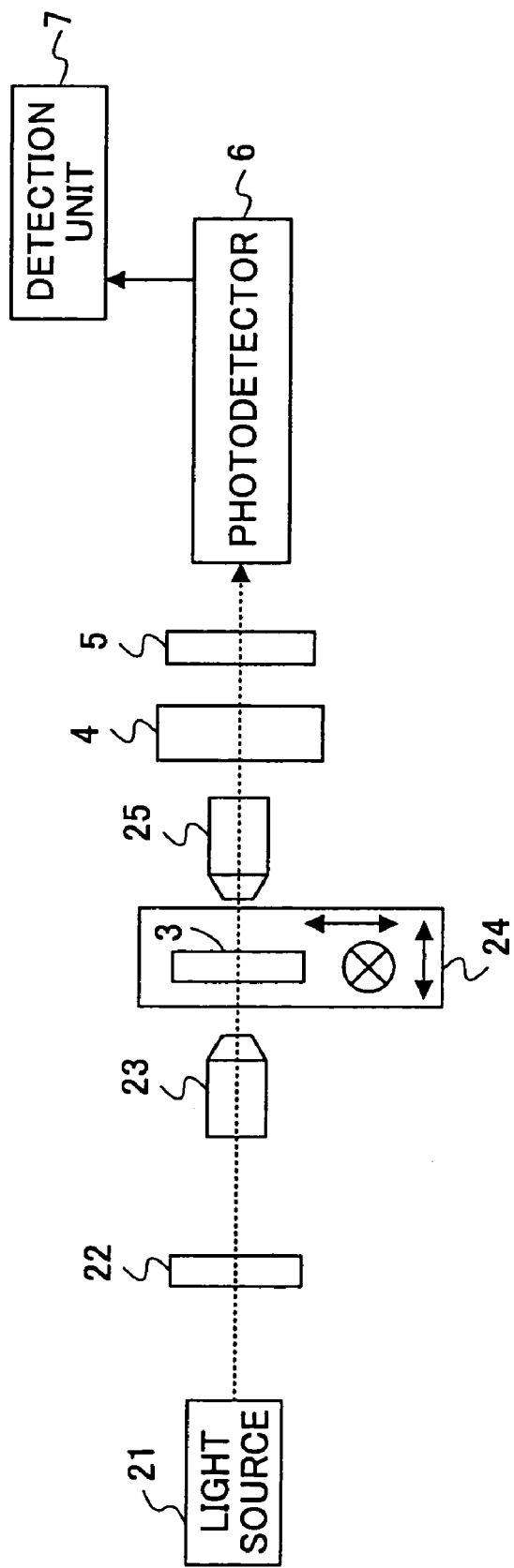
FIG. 14 is a block diagram of another preferred embodiment of the elastic-wave monitoring device of the present invention.

FIG. 14 shows the composition of the elastic-wave monitoring device in one embodiment of the present invention.

In the elastic-wave monitoring device shown in FIG. 14, the light source 21 is a laser (for example, a helium-neon laser with the wavelength 633 nm) of the linear polarization, and the laser light from the light source 21 passes through the ¼ wave plate 22, and the ¼ wave plate 22 converts the linearly polarized light into the circularly polarized light.

The laser light of the circular polarization is focused onto the surface of the measured object 3 by the objective lens 23.

The laser light passing through the crystal substrate of the measured object 3 is converted into the parallel light beam by the objective lens 25, and it passes through the compensating plate 4 and the polarizing filter 5 to the photodetector 6. With the compensating plate 4, the phase difference having occurred in the light beam by the natural double refraction of the crystal substrate is compensated. The light beam through the polarizing filter 5 is received by the photodetector 6, and the optical intensity of the light beam is detected by the photodetector 6.

The direction of the polarization transmission axis of the polarizing filter 5 in this embodiment is the same as that of the embodiment of FIG. 5.

In the elastic-wave monitoring device of FIG. 14, the periodic electrical signal is inputted to the measured object 3, and the frequency component of the output signal of the photodetector 6 that is the same as the frequency of the input signal is detected by the detection unit 7 which may be the spectrum analyzer. Hence, the elastic-wave monitoring device of this embodiment detects the distribution of the surface-acoustic-wave.

The measured object 3 is attached to the stage 24 which is movable in the three-dimensional manner, and the monitoring of the distribution of the elastic wave in the measured object 3 is performed by scanning the focus location of the objective lens 23 on the front surface of the measured object 3. Therefore, the elastic-wave monitoring device of this embodiment can monitor the 2-dimensional distribution of the surface-acoustic-wave in the measured object 3.

Figure 15:
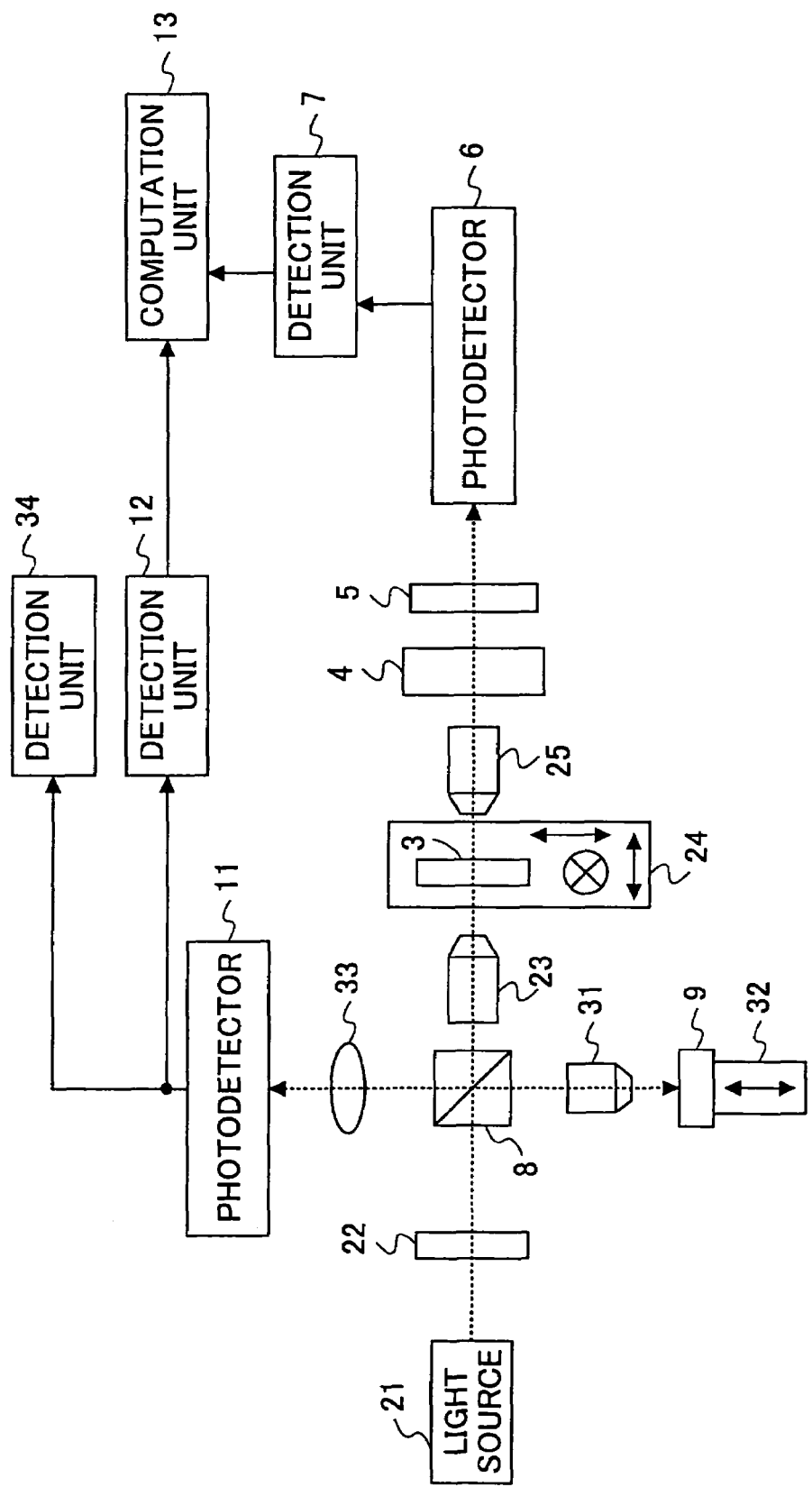
FIG. 15 is a block diagram of another preferred embodiment of the elastic-wave monitoring device of the present invention.

FIG. 15 shows the composition of the elastic-wave monitoring device in another embodiment of the present invention.

As shown in FIG. 15, the light of the linear polarization from the light source 21 is converted into the circularly polarized light by using the ¼ wave plate 22.

The circularly polarized light from the ¼ wave plate 22 is separated by the beam splitter 8 into the two light beams, and one of the light beams is focused on the measured object 3 by the objective lens 23, and the other light beam is focused on the reference mirror 9 by the objective lens 31.

The light beam reflected from the front surface of the measured object 3 and the light beam reflected by the reference mirror 9 are coupled together by the beam splitter 8, this coupled light beam is focused on the photodetector 11 by the lens 33, and the optical intensity of the coupled light beam is detected by the photodetector 11.

On the other hand, the light beam through the crystal substrate of the measured object 3 among the light focused to the measured object 3 is converted into the parallel light by the objective lens 25, and it passes through the compensating plate 4 and the polarizing filter 5 to the photodetector 6. The photodetector 6 detects the optical intensity of the resulting light.

Moreover, in the elastic-wave monitoring device of FIG. 15, the reflective mirror 9 is attached to the one-dimensional stage 32, and the location of the mirror 9 can be moved in the direction of the optical path.

Since the stroke of the stage 32 that corresponds to high-speed operation is about 10 micrometers, the stage 32 is preferably the stage using the piezoelectric element.

With the measured object 3, the surface-acoustic-wave measurement is performed while it is fixed to the 3-dimensional stage 24 and scanning the focus location of the objective lens 23 on the front surface, and can monitor the 2-dimensional distribution of the surface acoustic wave.

Moreover, in a case of the measurement by the interferometer, the movement of the stage 32 in which the reference mirror 9 is attached realizes the optical path difference of the sensibility maximum at each point, and the 2-dimensional scanning is performed.

In the elastic-wave monitoring device of FIG. 15, by the above-mentioned composition, the signal produced from the elastic-optical effects can be obtained from the output of the photodetector 6, and the signal of the perpendicular displacement component by the interference measurement can be acquired from the output of the photodetector 11.

The monitoring of each distribution of the two signals and the operation of the computation unit 13 which carries out the computations based on the two signals allow the monitoring of the distribution of the elastic wave obtained only from the on-surface component.

Moreover, the focus location of the objective lens 23 is matched with the front surface of the measured object 3 by adjusting the position of the stage 24 to the position where the maximum intensity change by interference occurs, when the stage 24 with the measured object 3 being attached is moved in the length-wise direction of the optical path.

Figure 16:
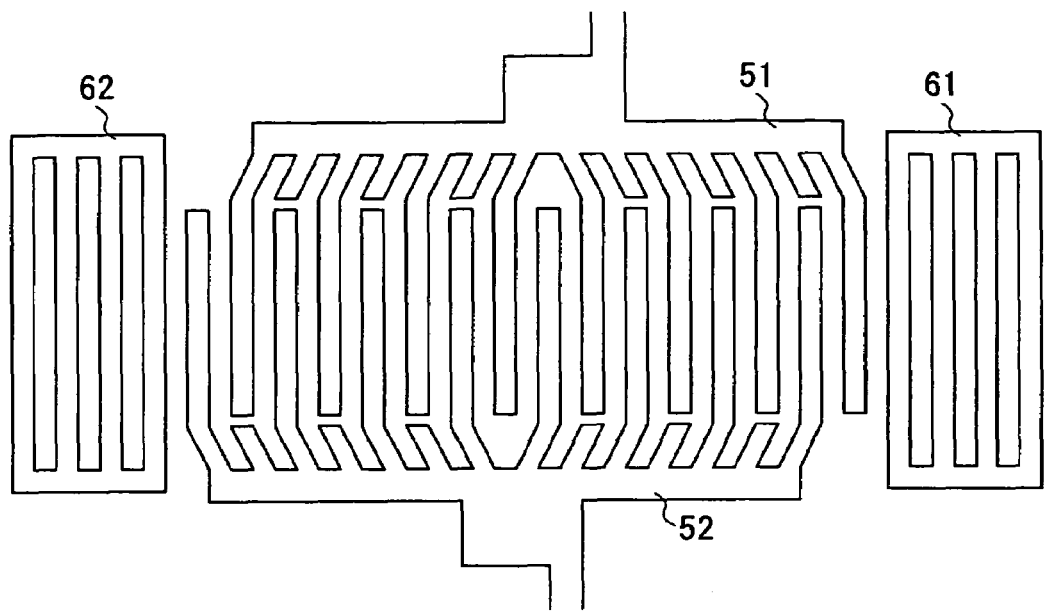
FIG. 16 is a diagram of an IDT electrode and reflectors used in one embodiment of the surface-acoustic-wave device of the present invention.

FIG. 16 shows an IDT electrode and the reflectors which are used in one embodiment of the surface-acoustic-wave device of the present invention.

As shown in FIG. 16, in the surface-acoustic-wave device of this embodiment, it includes the reflectors 61 and 62 with the comb-shaped electrodes 51 and 52 with the electrode finger which gave the include angle to the part of the root.

In the surface-acoustic-wave device of this embodiment, the comb-shaped electrodes 51 and 52 have the same composition as the IDT electrode shown in FIG. 12, and the reflectors 61 and 62 have the same composition as the conventional reflector shown in FIG. 10.

As explained above, the conventional elastic-wave monitoring method and the elastic-wave monitoring device and method of this embodiment relate to the technique which detects the distribution of the elastic wave from the change of the polarization state of the light which passes through the SAW device substrate.

Figure 19:
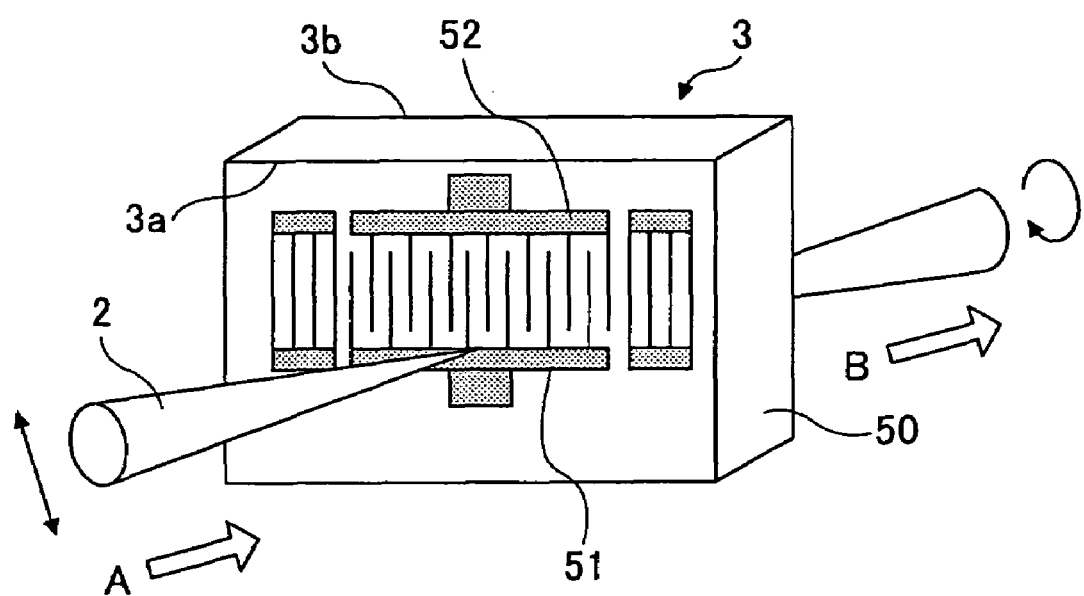
FIG. 19 is a diagram for explaining a conventional elastic-wave monitoring method.

For example, FIG. 19 shows a conventional elastic-wave monitoring method.

As shown in FIG. 19, in the conventional elastic-wave monitoring method, in the direction indicated by the arrow A, the light 2 is incident to the piezoelectric substrate 3 (the measured object) containing the piezoelectric crystal 50 and the metal electrodes 51 and 52. The transmission light through the piezoelectric substrate 3 is incident to the photodetector in the direction indicated by the arrow B, and the change of the polarization state of the transmission light is thus detected.

It is possible to monitor the surface-acoustic-wave distribution in the SAW device by detecting the change of the polarization state of the transmission light according to the conventional elastic-wave monitoring method. However, there is the problem that the behavior of the elastic wave in the non-sensitive region which the light does not pass through the SAW device (for example, the metal-electrode range) cannot be observed.

The metal electrode of the SAW device functions as the so-called mirror, and the incident light is reflected in the metal-electrode range of the SAW device. In the metal-electrode range, the incident light does not interact with the crystal of the SAW device substrate, and it becomes the non-sensitive region which the light does not pass through the SAW device.

In order to eliminate the above problem, the elastic-wave monitoring device and method of the present invention are configured such that they are able to monitor the surface-acoustic-wave distribution in all the ranges in the SAW device without any non-sensitive region, and to observe the behavior of the surface acoustic wave more precisely, which will be explained in the following.

Figure 17:
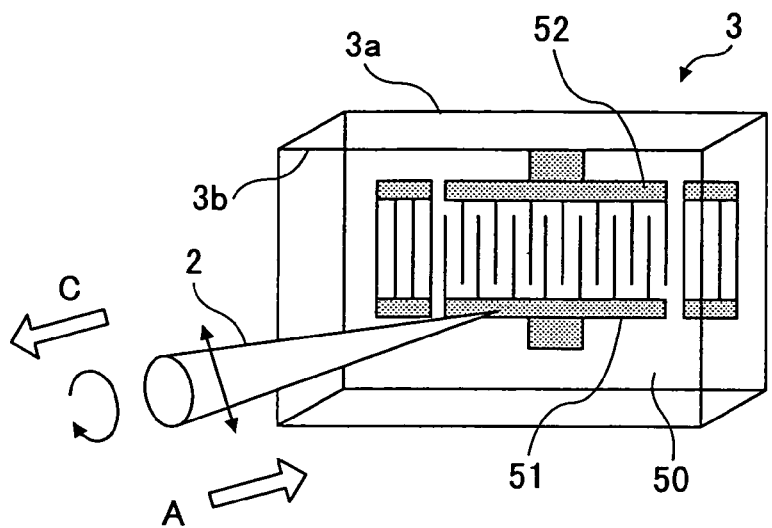
FIG. 17 is a diagram for explaining one embodiment of the elastic-wave monitoring method of the present invention.

FIG. 17 shows one embodiment of the elastic-wave monitoring method of the present invention.

In the elastic-wave monitoring method of FIG. 17, the elastic-wave monitoring device is configured so that the metal electrodes 51 and 52 are formed on the front surface 3a of the piezoelectric substrate 3 (the measured object) which includes the piezoelectric crystal 50 and the metal electrodes 51 and 52, and the circularly polarized light 2 is incident to the back surface 3b of the piezoelectric substrate 3 on which they are not formed.

In this embodiment, in order to prevent the scattered reflection of the light incident to the back surface 3b, the back surface 3b of the piezoelectric substrate 3 is ground beforehand.

The circularly polarized light 2 is incident to the back surface 3b of the piezoelectric substrate 3 in the direction indicated by the arrow A, and it is reflected by the interface between the metal electrodes 51 and 52 of the front surface 3a of the piezoelectric substrate 3 and the piezoelectric crystal 50, in the direction indicated by the arrow C so that the reflected light beam is incident to the photodetector. Thus, the change of the polarization state of the reflected light beam is detected.

In the elastic-wave monitoring method of FIG. 17, the metal electrodes 51 and 52 may function as the so-called mirror but may not disturb the polarization state by itself, the change of the polarization state of the reflected light beam detected by the photodetector depends on the intensity of the surface acoustic wave in the corresponding light irradiation location.

In addition, the change of the polarization state is detected as an optical intensity change of the light which is selected by the analyzer.

In the composition of FIG. 17, it is possible to carry out the monitoring of the distribution of the elastic wave under the metal electrode region of the piezoelectric substrate 3 which is impossible to monitor with the conventional elastic-wave monitoring method.

However, in the elastic-wave monitoring method of FIG. 17, in the range containing no metal electrode of the piezoelectric substrate 3, the difference in the index of refraction between the air and the piezoelectric substrate interface is small, and the reflectivity is low. Hence, it becomes a low sensibility range, and there is the problem that the monitoring of the distribution of the elastic wave in the whole SAW device is difficult.

Figure 18:
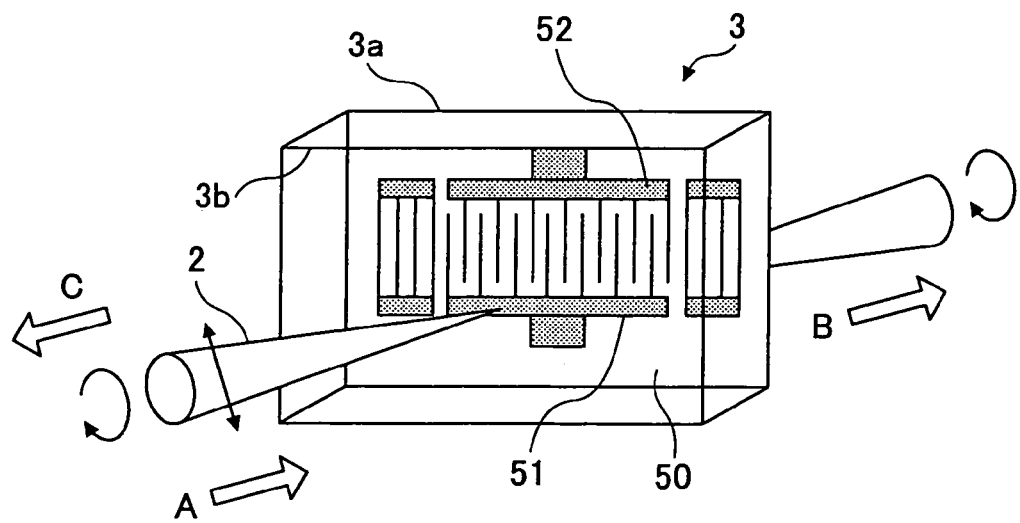
FIG. 18 is a diagram for explaining a modification of the elastic-wave monitoring method of FIG. 17.

FIG. 18 shows a modification of the elastic-wave monitoring method of FIG. 17.

The elastic-wave monitoring method of FIG. 18 is constituted in order to eliminate the above problem in the composition of FIG. 17.

Similar to the composition of FIG. 17, the metal electrodes 51 and 52 are formed on the front surface 3a of the piezoelectric substrate 3 (the measured object) which includes the piezoelectric crystal 50 and the metal electrodes 51 and 52, and electrodes are not formed on the back surface 3b of the piezoelectric substrate 3. The light 2 is incident to the back surface 3b of the piezoelectric substrate 3.

In the elastic-wave monitoring method of FIG. 18, the first polarization analysis optical system and the second polarization analysis optical system are provided.

In the first polarization analysis optical system, the incidence of the light 2 is made in the direction indicated by the arrow A to the back surface 3b of the piezoelectric substrate 3, and the change of the polarization state of the reflected light beam reflected by the interface between the metal electrodes 51 and 52 and the piezoelectric crystal 50 on the front surface 3a of the piezoelectric substrate 3 in the direction indicated by the arrow C is detected.

The lens, the reflective mirror, the analyzer, the photodetector, etc. for detecting the polarization state of the reflected light beam are contained in the first polarization analysis optical system.

Moreover, in the second polarization analysis optical system, the change of the polarization state of the transmission light which passes through the range of the piezoelectric crystal 50 in the direction shown by the arrow B where the metal electrodes 51 and 52 on the front surface 3a of the piezoelectric substrate 3 are not formed is detected.

The lens, the analyzer, the photodetector, etc. for detecting the polarization state of transmission light are contained in the second polarization analysis optical system.

In the composition of FIG. 18, using the output signal of the first polarization analysis optical system allows the monitoring of the distribution of the elastic wave in the non-sensitive region of the SAW device in which the light is reflected by the interface of the metal electrodes 51 and 52 and the piezoelectric crystal 50, while using the output signal of the second polarization analysis optical system allows the monitoring of the distribution of the elastic wave in the range between the metal electrode 51 and 52, etc. in which the light passes through the SAW device. Therefore, it is possible to monitor the distribution of the elastic wave in all the ranges of the SAW device, such as the piezoelectric substrate 3, without any non-sensitive region.

However, the signal intensity of the output signal from the first polarization analysis optical system based on the reflected light and the signal intensity of the output signal from the second polarization analysis optical system based on the transmission light are not necessarily in agreement, and a certain compensation is needed.

The transmission light can be considered as interacting only once, but the reflected light from the metal electrode can be considered as interacting with the elastic wave two times and quantities of the reflected light and transmission light are different. These seem to be a major cause that the signal intensity of the output signal from the first polarization analysis optical system based on the reflected light is not in agreement with the signal intensity of the output signal from the second polarization analysis optical system based on the transmission light.

What is necessary to cancel the problem is to multiply both the output signals by a predetermined correction factor, and just to add the compensation, in order to give the uniqueness between the output signals of both the optical systems.

The multiplication for this compensation is performed after acquisition of observation data on the computer.

Or it is also possible to input the output signal of both the analyses optical system into the exclusive circuit, and to perform the multiplication for the compensation in the exclusive circuit.

The piezoelectric crystal used as the SAW device substrate has the limited index of refraction, and produces optical reflection of what minute also in the interface with the air.

For example, the reflectivity of LiTaO3 which is the typical piezoelectric crystal is about 13%.

Therefore, in the range which the light between the metal electrodes passes through, detection of the surface-acoustic-wave is possible by the first polarization analysis optical system using the reflected light beam.

The output signal from this first polarization analysis optical system determines that the correction factor is in agreement with the output signal from the second polarization analysis optical system using transmission light.

However, before determining the correction factor, the amount of signals is divided by the quantity of light which is received with each optical system, and it is necessary to compensate the quantity-of-light dependency.

Thus, by using the determined correction factor, it becomes possible to give uniqueness between the output signals from two polarization analysis optical systems.

Therefore, it becomes possible to observe and visualize the surface-acoustic-wave distribution in all the ranges of the SAW device. The method of determining the above-mentioned correction factor will be described later.

Figure 20:
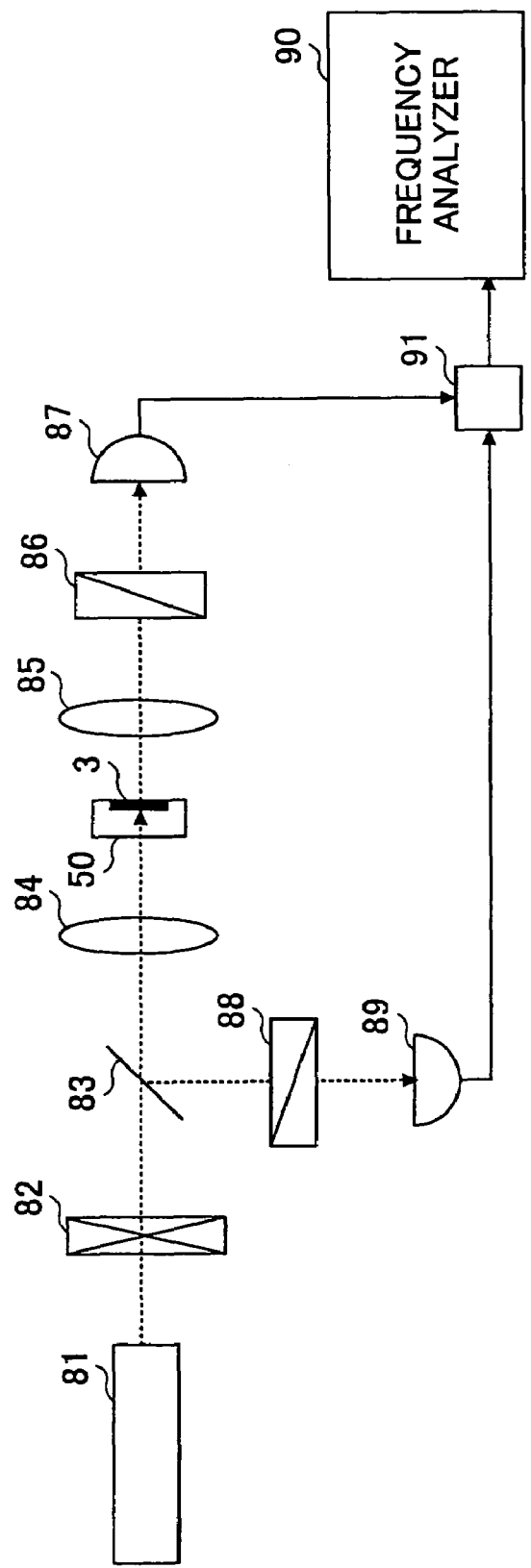
FIG. 20 is a block diagram of another preferred embodiment of the elastic-wave monitoring device of the present invention.

FIG. 20 shows another preferred embodiment of the elastic-wave monitoring device of the present invention.

In order to observe the distribution of the elastic wave which exists in the SAW device, especially that of the SH wave, without the non-sensitive region, the elastic-wave monitoring device of this embodiment is provided with the monitoring optical system and the signal compensation unit.

Similar to the composition of FIG. 18, in the elastic-wave monitoring device of FIG. 20, the metal electrode is formed on the front surface 3a of the piezoelectric substrate 3 (the SAW device) which includes the piezoelectric crystal 50, and the light from the light source is incident to the back surface 3b in which the metal electrode is not formed.

In the composition of FIG. 20, the monitoring optical system to the piezoelectric substrate 3 includes the monochromatic light source (for example, a laser light source) 81, the polarization adjustment optical system 82 which adjusts the polarization state to the desired state, the first polarization analysis optical system using the reflected light beam from the piezoelectric substrate 3, and the second polarization analysis optical system using the transmission light through the piezoelectric substrate 3.

The half mirror 83, the lens 84, the analyzer 88, and the photodetector 89 are contained in the first polarization analysis optical system.

While the lens 84 focuses the laser light from the light source 81 on the metal electrode of the piezoelectric substrate 3, it collimates the reflected light beam from the piezoelectric substrate 3.

The half mirror 83 passes part of the laser light from the light source 81 and turns the light that is reflected from the piezoelectric substrate 3 to the analyzer 88 partially.

The laser light through the analyzer 88 is incident to the photodetector 89, and the photodetector 89 outputs the signal which indicates the change of the polarization state of the reflected light beam.

The lens 85, the analyzer 86, and the photodetector 87 are contained in the second polarization analysis optical system.

The lens 85 collimates again the laser light which penetrated the piezoelectric substrate 3.

The laser light through the analyzer 86 is incident to the photodetector 87 and the photodetector 87 outputs the signal which indicates the change of the polarization state of the transmission light.

Furthermore, the monitoring optical system of FIG. 20 includes the scanning mechanism (not shown) which moves the piezoelectric substrate 3 in the direction which intersects perpendicularly to the direction of the optical axis of laser light, in order to change the optical incidence location in the SAW device 3.

Moreover, the elastic-wave monitoring device of FIG. 20 is provided with the source (not shown) of the drive signal for applying the drive electrical potential difference between the metal electrodes 51 and 52 of the SAW device 3.

In the elastic-wave monitoring device of FIG. 20, the signal analysis of the output signals from the first and second polarization analysis optical systems is carried out by the signal compensation unit.

The signal compensation unit includes the switches 91, and through the switches 91, either the output signal of the first polarization analysis optical system or the output signal of the second polarization analysis optical system is supplied to the frequency analyzer 90 which performs signal analysis.

In the composition of FIG. 20, although it is suitable for the above-mentioned signal analysis to use the frequency analyzer 90, it is not limited to this embodiment.

The change timing of the switch 91 synchronizes with the change timing of the laser light irradiation location, it judges whether the incidence location of laser light is the metal-electrode side, and it is changed.

Control of this change timing and the judgment of the laser light incidence location are performed in the control unit which is not illustrated.

For example, when it is determined with the incidence location of the laser light being the metal-electrode side, the control unit changes the switch 91, and it controls it so that the output signal from the photodetector 89 is supplied to the frequency analyzer 90.

When it is determined with the incidence location of the laser light not being the metal-electrode side, the control unit changes the switch 91, and it controls it so that the output signal from the photodetector 87 is supplied to the frequency analyzer 90.

It is also possible to control the switching timing of the switch 91 so that, unlike the previously described control system, the control unit measures the quantity of the received light based on the output signal from the first and second polarization analysis optical systems and chooses simply the one where the light-receiving quantity of light is larger in the composition of FIG. 20.

In this case, it is required to rectify the data collected after the signal analysis one by one on the computer.

The calculation procedure of the correction factor for this compensation will be described later.

As explained above, according to the elastic-wave monitoring device of FIG. 20, it is possible to monitor and visualize the intensity distribution of an elastic wave in all the ranges of the SAW device without any non-sensitive region.

Figure 21:
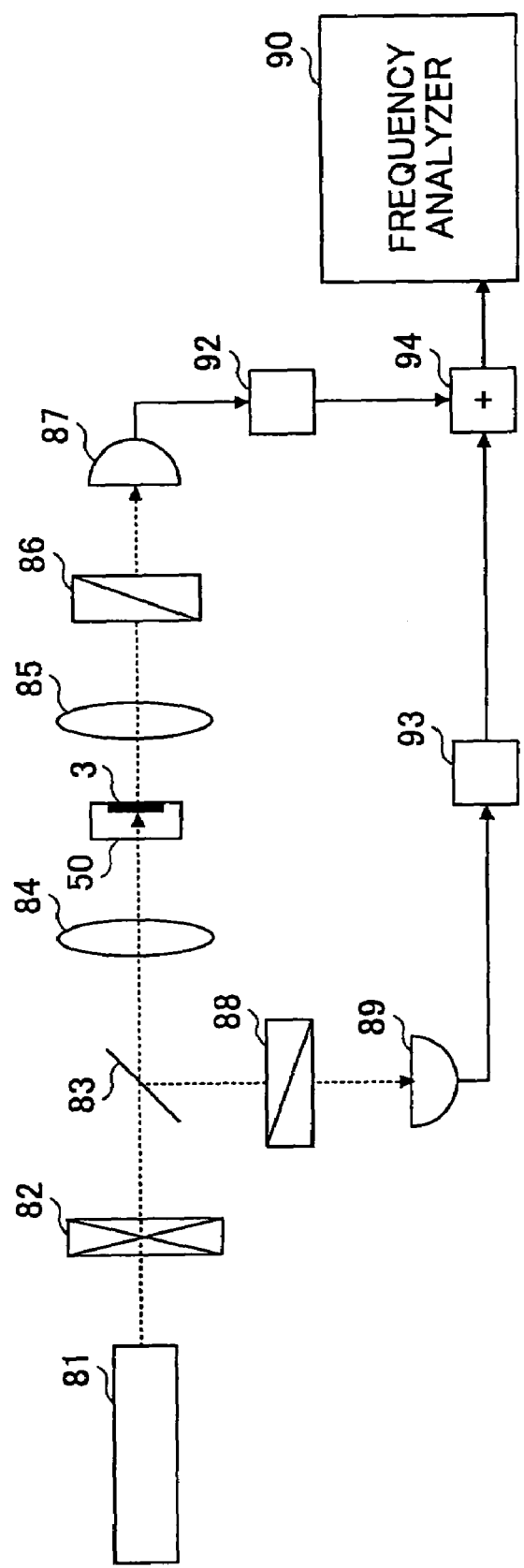
FIG. 21 is a block diagram of a modification of the elastic-wave monitoring device of FIG. 20.

FIG. 21 shows a modification of the elastic-wave monitoring device of FIG. 20.

In order to monitor the intensity distribution of the elastic wave in the SAW device (especially, that of the SH wave) without any non-sensitive region, the elastic-wave monitoring device of this embodiment is provided with the monitoring optical system and the signal compensation unit.

In the elastic-wave monitoring device of FIG. 21, the monitoring optical system with respect to the piezoelectric substrate 3 is the same as that of the composition of FIG. 20, and a description thereof will be omitted.

In the composition of FIG. 21, the signal compensation unit includes the first compensation circuit 93 which corrects the output signal of the photodetector 89 based on the reflected light beam, the second compensation circuit 92 which corrects the output signal of the photodetector 87 based on the transmission light, and the adder 94 which outputs the sum of the outputs of the two compensation circuits 92 and 93.

In the composition of FIG. 21, the output signals from the first and second polarization analysis optical systems are corrected by the first and second compensation circuits 93 and 92, respectively. The resulting signals after the correction are added together by the adder 94. The adder 94 outputs a signal indicating the sum of the corrected signals from the first and second compensation circuits 93 and 92, to the input of the frequency analyzer 90. The frequency analyzer 90 performs the signal analysis of the output signal from the adder 94.

In the elastic-wave monitoring device of FIG. 21, the output signals from the first and second polarization analysis optical systems are corrected by the first and second compensation circuits 93 and 92. Each of such correction processes is performed at the first and second compensation circuits 93 and 92 by multiplication of a predetermined correction factor. Then, the adder 94 supplies the signal indicating the sum of the corrected signals from the first and second compensation circuits 93 and 92, to the frequency analyzer 90.

According to this embodiment, the operation processing load on the computer can be reduced, and the monitoring of the large-scale SAW device with many data points can be carried out efficiently.

Next, the calculation procedure of the correction factor used by the first and second compensation circuits 93 and 92 will now be described.

For the sake of simplicity of description, only the one-dimensional surface-acoustic-wave distribution will be considered in the following. However, it is clear that the case of the two-dimensional surface-acoustic-wave distribution can also be considered in the same way.

When a light beam passes through an elastic wave in a crystal substrate, it is slightly modulated. It is necessary that the elastic-wave monitoring device detect only this modulation condition of the light beam. Therefore, the signal intensity SIGNAL is proportional to the intensity $S(x)$ of the elastic wave and the quantity Io of the received light beam, and it is represented by the formula:

SIGNAL=$m \times Io$ where $m=k \times S(x)$ ($m=10^{-3}$ to $10^{-4}$)

The technical terms used here are defined as follows: $S(x)$ indicates the distribution of the intensity of the elastic wave; Rm shows the reflectivity of the electrode metal; Rc indicates the reflectivity of the front surface of the crystal (in the case of the piezoelectric crystal $LiTaO_3$, Rc is about 13%); Tc shows the permeability of the front surface of the crystal (Tc=1−Rc); Ii indicates the intensity (constant) of the incident light; Ior(x) indicates the quantity of the received light on the side of the reflected light; Iot(x) indicates the quantity of the received light on by the side of the transmission light; C1 indicates the predetermined correction factor which is used by the first compensation circuit 93; C2 indicates the predetermined correction factor which is used by the second compensation circuit 92; Lr indicates the rate of the quantity-of-light loss of the measurement optical path on the side of the reflected light; and Lt indicates the rate of the quantity-of-light loss of the measurement optical path on the side of the transmission light.

Moreover, x=0 shows the metal-electrode side, and x=1 shows the piezoelectric-crystal side.

The reflectivity of the metal-electrode surface in the SAW device and the reflectivity of the front surface of the crystal differ from each other when the measurement is performed only with the output signal of the first polarization analysis optical system based on the reflected light beam. The quantities of the light beams received by the photodetectors differ greatly, and there is the possibility that discontinuity may arise in the distribution of the elastic wave which is finally obtained by the elastic-wave monitoring device.

To avoid the above problem, the output signal of the second polarization analysis optical system based on the transmission light is also used, and a certain correction of the output signal of each optical system is required because the optical systems are different.

For this reason, the correction factors C1 and C2 for the two optical systems are computed as follows.

The signal intensity SIGNAL(0) obtained by receiving the reflected light beam from the metal-electrode surface of the piezoelectric crystal 3 (the SAW device) is expressed by the following formula (1):

$$\text{SIGNAL}(0) = 2 \times m(0) \times Ior(0) \qquad (1)$$
$$= 2 \times k \times S(0) \times Lr \times Rm \times Ii$$

In the above formula (1), the multiplier "2" is used since the light goes through and comes back to the inside of the piezoelectric crystal 50.

On the other hand, the signal intensity SIGNAL(1)_r obtained by receiving the reflected light beam from the front surface of the crystal is expressed by the following formula (2):

$$\text{SIGNAL}(1)\_r = 2 \times m(1) \times Ior(1) \qquad (2)$$
$$= 2 \times k \times S(1) \times Lr \times Rc \times Ii$$

Moreover, the signal intensity SIGNAL(1)_t obtained by receiving the transmission light is expressed by the following formula (3):

$$\text{SIGNAL}(1)\_t = m(1) \times Iot(1) \qquad (3)$$
$$= k \times S(1) \times Lt \times Tc \times Ii$$
$$= k \times S(1) \times Lt \times (1 - Rc) \times Ii$$

From the above formulas (2) and (3), the relation between SIGNAL(1)_r and SIGNAL(1)_t is obtained as follows.

$$S(1) = \text{SIGNAL}(1)\_r / (2 \times k \times Lr \times Rc \times Ii)$$
$$= \text{SIGNAL}(1)\_t / (k \times Lt \times (1 - Rc) \times Ii)$$

$$C1 = \text{SIGNAL}(1)\_t / \text{SIGNAL}(1)\_r$$
$$= (k \times Lt \times (1 - Rc) \times Ii) / (2 \times k \times Lr \times Rc \times Ii)$$
$$= Lt \times (1 - Rc) / (2 \times Lr \times Rc)$$

When the first correction factor C1 by the above formula is used and the incident light hits the crystal surface, it is possible to improve the detection sensibility of the elastic wave by using the output signal of the photodetector 87 on the side of the transmission light which is large in the quantity of the received light.

Next, when the elastic wave of the same intensity exists on the front surface of the crystal and the bottom of the metal electrode (in the case of S(0)=S(1)), it is required that the signal intensities obtained from the different optical systems are the same.

That is, when S(0)=S(1), the signal intensities obtained from the different optical systems must satisfy the relation SIGNAL(0)=SIGNAL(1)_r=SIGNAL(1)_t/C1. It is necessary to introduce the second correction factor C2 which is expressed by the following formula:

$$2 \times m(0) \times Ior(0) = 2 \times m(0) \times Ior(1) \times C2$$
$$= m(0) \times Iot(1) \times C2/C1$$

where C2 is computed by the formula C2=Ior(0)/Ior (1) as a ratio of the quantity of the total received light.

Accordingly, in the elastic-wave monitoring device of FIG. 21, the first compensation circuit 93 is configured as the amplifier having the amplification degree 1, and the second compensation circuit 92 is configured as the amplifier having the amplification degree: C2×(1+C1)/C1.

As described above, the output signal of the first compensation circuit 93 and the output signal of the second compensation circuit 92 are added together by the adder 94. By supplying the output signal of the adder 94 to the frequency analyzer 90, the elastic-wave monitoring device of this embodiment can always provide a stable detection sensibility of the distribution of an elastic wave.

In addition, the composition of the above-mentioned compensation circuits 92 and 93 is shown as one embodiment, and the present invention is not limited only to the above-mentioned embodiment. Even if another composition of the compensation circuits 92 and 93 is used, it is clear that similar advantages of the present invention are obtained.

As explained above, according to the elastic-wave monitoring device and method of the present embodiment, it is possible to monitor the distribution of the elastic wave in all the ranges in the SAW device without creating any non-sensitive region, and to observe the behavior of the elastic wave more precisely.

The present invention is not limited to the above-described embodiments, and variations and modifications may be made without departing from the scope of the present invention.

What is claimed is:

1. A surface-acoustic-wave device comprising:
a piezoelectric substrate; and
first and second comb-shaped electrodes each having a bus-bar portion parallel to a propagation direction of a surface acoustic wave in the substrate, and respective electrode fingers periodically formed on the piezoelectric substrate and extending in directions perpendicular to the propagation direction,
wherein the electrode fingers of the first comb-shaped electrode and the electrode fingers of the second comb-shaped electrode are separated away from the bus-bar portion of the opposing comb-shaped electrode, the respective electrode fingers being periodically arrayed in the propagation direction of the surface-acoustic-wave, and the electrode fingers of each comb-shaped electrode are inclined at root portions thereof outwardly right and left from the bus-bar portion of the corresponding comb-shaped electrode so that the inclined portions of the electrode fingers face a direction of a leaking surface-acoustic-wave perpendicularly.

2. The surface-acoustic-wave device of claim 1 wherein the first comb-shaped electrode includes first dummy electrodes at intermediate positions between two adjacent ones of the electrode fingers thereof, the first dummy electrodes connected to the bus-bar portion of the first comb-shaped electrode and opposing to leading edges of the electrode fingers of the second comb-shaped electrode respectively, and the second comb-shaped electrode includes second dummy electrodes at intermediate positions between two adjacent ones of the electrode fingers thereof, the second dummy electrodes connected to the bus-bar portion of the second comb-shaped electrode and opposing to leading edges of the electrode fingers of the first comb-shaped electrode respectively.

3. The surface-acoustic-wave device of claim 1 wherein the electrode fingers of the first comb-shaped electrode and the electrode fingers of the second comb-shaped electrode include straight-line portions which extend in a direction perpendicular to the propagation direction of the surface acoustic wave.

4. The surface-acoustic-wave device of claim 2 wherein each of the first dummy electrodes is inclined in parallel to the inclined portions of corresponding ones of the electrode fingers of the first comb-shaped electrode adjacent to and interposing the first dummy electrode, and each of the second dummy electrodes is inclined in parallel to the inclined portions of corresponding ones of the electrode fingers of the second comb-shaped electrode adjacent to and interposing the second dummy electrode.

5. A surface-acoustic-wave device comprising:
a piezoelectric substrate;
an inter-digital transducer provided on the piezoelectric substrate, the inter-digital transducer including first and second comb-shaped electrodes each having a bus-bar portion parallel to a propagation direction of a surface acoustic wave in the substrate, and respective electrode fingers periodically formed on the piezoelectric substrate and extending in directions perpendicular to the propagation direction; and
a pair of reflectors provided at a left edge and a right edge of the inter-digital transducer along the propagation direction, wherein the electrode fingers of the first comb-shaped electrode and the electrode fingers of the second comb-shaped electrode are separated away from the bus-bar portion of the opposing comb-shaped electrode, the respective electrode fingers being periodically arrayed in the propagation direction of the surface-acoustic-wave, and the electrode fingers of each comb-shaped electrode are inclined at root portions thereof outwardly right and left from the bus-bar portion of the corresponding comb-shaped electrode so that the inclined portions of the electrode fingers face a direction of a leaking surface-acoustic-wave perpendicularly.

6. The surface-acoustic-wave device of claim 5 wherein the piezoelectric substrate is constituted by single crystals of lithium tantalate $LiTaO_3$, the substrate having a cut plane rotated around X axis by 36 to 46 degrees from Y axis to Z axis, and each of the reflectors including edge portions which are inclined by 8 to 15 degrees from a direction perpendicular to the propagation direction of the surface-acoustic-wave.

* * * * *